(12) United States Patent
Ferree

(10) Patent No.: US 7,156,848 B2
(45) Date of Patent: Jan. 2, 2007

(54) CHECK REINS FOR ARTIFICIAL DISC REPLACEMENTS

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 135 days.

(21) Appl. No.: 10/422,147

(22) Filed: Apr. 24, 2003

(65) Prior Publication Data
US 2003/0204271 A1    Oct. 30, 2003

Related U.S. Application Data

(63) Continuation-in-part of application No. 10/421,433, filed on Apr. 23, 2003.

(60) Provisional application No. 60/375,286, filed on Apr. 24, 2002.

(51) Int. Cl.
*A61B 17/70* (2006.01)
*A61F 2/44* (2006.01)

(52) U.S. Cl. .................... 606/61; 623/17.16

(58) Field of Classification Search .................. 606/61; 623/17.11, 17.12, 17.13, 17.14, 17.15, 17.16
See application file for complete search history.

(56) References Cited

U.S. PATENT DOCUMENTS

| | | | |
|---|---|---|---|
| 3,867,728 A | 2/1975 | Stubstad et al. ................... 3/1 |
| 4,911,718 A | 3/1990 | Lee et al. ..................... 623/17 |
| 5,171,281 A | 12/1992 | Parsons et al. ............... 623/17 |
| 5,258,031 A | 11/1993 | Salib et al. .................... 623/17 |
| 5,425,773 A | 6/1995 | Boyd et al. .................... 623/17 |
| 5,545,229 A | 8/1996 | Parsons et al. ............... 623/17 |
| 5,562,738 A | 10/1996 | Boyd et al. .................... 623/17 |
| 5,674,296 A * | 10/1997 | Bryan et al. ............. 623/17.16 |
| 6,063,121 A | 5/2000 | Xavier et al. ................. 623/17 |
| 6,540,785 B1 | 4/2003 | Gill et al. ................ 623/17.14 |

\* cited by examiner

*Primary Examiner*—Cris L. Rodriguez
*Assistant Examiner*—Candice C. Stokes
(74) *Attorney, Agent, or Firm*—Gifford, Krass, Groh, Sprinkle, Anderson & Citkowski, PC

(57) ABSTRACT

Check reins in the form of elongated members are used to limit the extreme range of motion which would otherwise be permitted by some ADR designs. The check reins serve two main purposes. First, they retain disc spacers, if present. Additionally, the wedge shape of ADRs and the removal of the Anterior Longitudinal Ligament (ALL) and a portion of the Annulus Fibrosus (AF) to insert the ADR from an anterior approach, favor anterior extrusion of disc spacers. In preferred embodiments the check reins are therefore limited to the anterior portion of the periphery of the ADR. Second, check reins serve to prevent excessive spinal motion. Again, although they may be helpful in other locations, anterior check reins help restore the motion limiting functions of the ALL and AF that were removed in anterior approaches to the spine.

11 Claims, 1 Drawing Sheet

CHECK REINS FOR ARTIFICIAL DISC REPLACEMENTS

REFERENCE TO RELATED APPLICATION

This application claims priority from U.S. Provisional Patent Application Ser. No. 60/375,286, filed Apr. 24, 2002, and is a continuation-in-part of U.S. Patent Application Ser. No. 10/421,433, filed Apr. 23, 2003. The entire content of each application is incorporated herein by reference.

FIELD OF THE INVENTION

This invention relates generally to artificial disc replacements (ADRs) and, more particularly, to check reins for ADRs.

BACKGROUND OF THE INVENTION

Replacement of cervical discs with synthetic devices that preserve motion could destabilize the cervical spine. Trauma to a destabilized cervical spine could cause spine cord injury. Insertion of most types of artificial disc replacements (ADR) requires cutting the anterior longitudinal ligament and removal of a portion of the anterior half of the annulus fibrosis and nucleus pulposus. Weakening the supporting structures on the anterior portion of the spine increases the probability of spinal cord injury with excessive force from a posterior direction. For example, a patient with an ADR in the cervical spine could become paralyzed from "whiplash" resulting from a motor vehicle accident.

Inventions do exist to help prevent the extrusion of ADR materials. For example, U.S. Pat. No. 6,063,121 teaches the use of x-shaped wires about the entire perimeter of the upper and lower plates. Lastly, '121 teaches the use of "wires" in a repeating X pattern. Our preferred embodiment of the device should include other, more flexible materials. Check reins made of inelastic, materials that do not flex well, will limit ADR motion excessively. Circumferential check reins must become lax, allowing the ADR Endplates to approach one another, to permit ADR motion. Repeated bending of wires risks injury to the surrounding tissues. First, the bend in stiff wires could impinge the surrounding tissues. Second, the tissues could be pierced by the ends of broken wires.

Similarly, U.S. Pat. No. 3,867,728 teaches the use of Dacron stitching in an X pattern about the periphery of ADRs. U.S. Pat. Nos. 4,911,718; 5,171,281; and 5,545,229 show the use of outer elastic membranes that are reinforced with fibers. The membranes are placed such that the reinforcement fibers are oriented in a crossing pattern between membranes.

SUMMARY OF THE INVENTION

This invention is broadly directed to check reins in the form of elongated members used to limit the extreme range of motion which would otherwise be permitted by some ADR designs. The check reins serve two main purposes. First, they retain disc spacers, if present. Additionally, the wedge shape of ADRs and the removal of the Anterior Longitudinal Ligament (ALL) and a portion of the Annulus Fibrosus (AF) to insert the ADR from an anterior approach, favor anterior extrusion of disc spacers. In preferred embodiments the check reins are therefore limited to the anterior portion of the periphery of the ADR. Second, check reins serve to prevent excessive spinal motion. Again, although they may be helpful in other locations, anterior check reins help restore the motion limiting functions of the ALL and AF that were removed in anterior approaches to the spine.

DETAILED DESCRIPTION OF THE INVENTION

The invention is broadly directed to check reins in the form of elongated members used to limit the extreme range of motion which would otherwise be permitted by some ADR designs. The check reins serve two main purposes. First, they retain disc spacers, if present. Additionally, the wedge shape of ADRs and the removal of the Anterior Longitudinal Ligament (ALL) and a portion of the Annulus Fibrosus (AF) to insert the ADR from an anterior approach, favor anterior extrusion of disc spacers. In preferred embodiments the check reins are therefore limited to the anterior portion of the periphery of the ADR.

Figure 2:
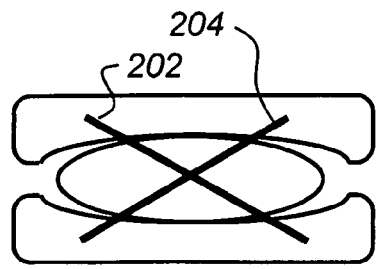
FIG. 2 illustrates the use of crossed check reins according to the invention.
Figure 5:
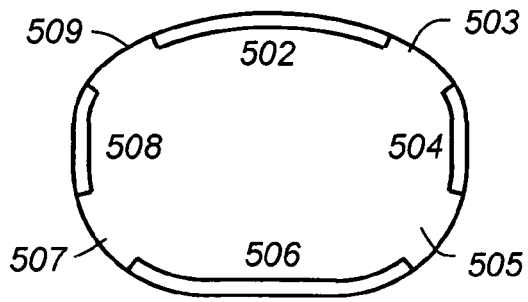
FIG. 5 is an axial cross section of the ADR of the present invention.

Second, check reins serve to prevent excessive spinal motion. Again, although they may be helpful in other locations, anterior check reins help restore the motion limiting functions of the ALL and AF that were removed in anterior approaches to the spine. As illustrated in FIG. 2, check reins may helpful in the anterior and posterior portions of ADRs. Check reins may also be used about all sides of the ADR. Note that it is not necessary according to the invention to have closely approximated check reins about the periphery of the ADR. Spaces between groups of check reins about the periphery of the ADR may allow ADRs to move better, as shown in FIG. 5.

Furthermore, in contrast to existing devices, elastic and more flexible or resilient designs are used in accordance with this invention. Braided materials, for example, are more flexible and have improved longevity. The braided materials could include wire filaments (cable), polymer filaments, or filaments of other biologically acceptable material. My co-pending U.S. Patent Application Ser. No. 10/421,433 teaches the use of biologic materials that may be used to form check reins according to this application. According to this embodiment, ligaments and/or bone are grafted from one vertebra to another vertebra. The reconstructed or augmented AF and ALL also help retain intradiscal devices and prevent excessive vertebral motion.

Figure 1:
FIG. 1 illustrates the use of check reins that are limited to one side of an artificial disc replacement (ADR)

Turning now to the drawings, FIG. 1 is a side-view drawing showing the use of an anterior check rein 102 to prevent extension, for example. Lateral check reins may be used to prevent lateral bending, and cross-coupled check reins may be used to prevent translation. FIG. 2 depicts the use of cross-coupled check reins 202, 204.

Figure 3:
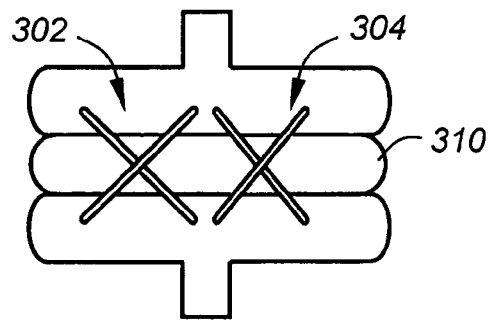
FIG. 3 is a view of the anterior aspect of an ADR and an alternative embodiment of the invention.
Figure 4A:
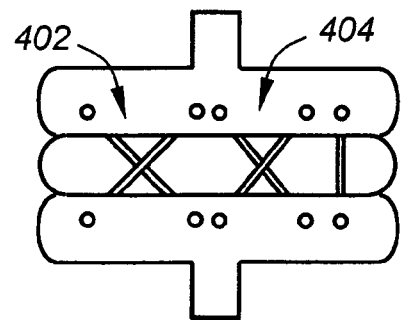
FIG. 4A is a view of the anterior aspect of an ADR and an alternative embodiment of the device.

FIG. 3 is a view of the anterior aspect of an ADR and an alternative embodiment of the invention. Multiple crossed check reins 302, 304 are illustrated on the anterior aspect of the ADR 310. FIG. 4A is a view of the anterior aspect of an ADR and an alternative embodiment of the device. Multiple check reins are illustrated. Some of the check reins cross. The check reins 402, 404 can be assembled and tightened in-situ.

Figure 4B:
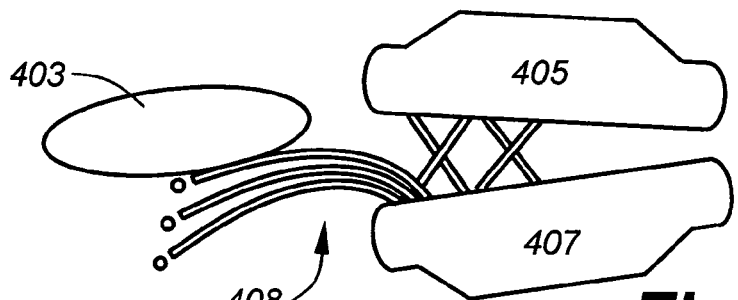
FIG. 4B is an exploded view of the lateral aspect of the ADR shown in FIG. 4A.

FIG. 4B is an exploded view of the lateral aspect of the ADR drawn in FIG. 4A. A disc spacer 403 is seen anterior to the ADR endplates 405, 407. Some of the check reins have been connected to both of the ADR EPs. Other check reins 408 are connected to only the bottom ADR EP. The loose check reins will be threaded to the upper ADR EP after the disc spacer is inserted. In-situ assembly of the check reins eases insertion of the disc spacer. In-situ assembly also allows surgeons to select the optimal tension on the check reins.

Figure 4C:
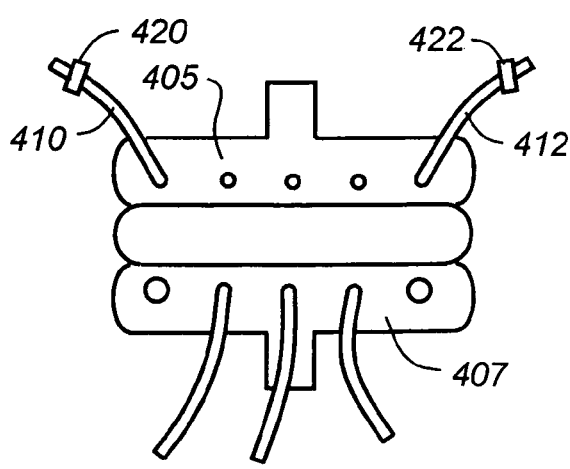
FIG. 4C is a view of the anterior aspect of an ADR and the embodiment of the ADR shown in FIG. 4B.

FIG. 4C is a view of the anterior aspect of an ADR and the embodiment of the ADR drawn in FIG. 4B. The disc spacer 403 has been inserted between the ADR EPs 405, 409. Two of the check reins 410, 412 are shown threaded through both ADR EPs. The check reins can be tightened and locked into position by crimping components 420, 422 that slide over the check reins. The excess check rein can be cut and removed after the final tightening of the check reins.

FIG. 5 is an axial cross section of an ADR. The areas 502, 504, 506, 508 of the drawing represent potential locations for check reins in one embodiment of the device. Gaps 503, 505, 507, 509 between groups of check reins facilitate ADR motion. Other embodiment of the device may group check reins in other location about the periphery of the ADR.

I claim:

1. Apparatus for stabilizing an artificial disc replacement (ADR), comprising:
    upper and lower spaced-apart endplate components, each adapted for attachment to a respective one of the upper and lower vertebrae to define a space therebetween, the endplate components having anterior, lateral, and posterior peripheral regions;
    a mobile member disposed in the space between the endplate components, the member being unconnected and free to move from side-to-side within the space; and
    one or more elongated elements within the space and spanning the anterior peripheral region, each element having two ends, one affixed to the upper endplate component, and another affixed to the lower endplate component to keep the mobile member from sliding out of the space at least in the anterior direction.

2. The apparatus of claim 1, wherein the elongated elements are at least partially elastic.

3. The apparatus of claim 1, including at least two elongated elements that cross one another.

4. The apparatus of claim 1, including at least one of the elongated elements is tightened in-situ.

5. The apparatus of claim 1, including at least one of the elongated elements is braided.

6. Apparatus for stabilizing an artificial disc replacement (ADR), comprising:
    upper and lower spaced-apart endplate components, each adapted for attachment to a respective one of the upper and lower vertebrae to define a space therebetween, the endplate components having anterior, lateral, and posterior peripheral regions;
    a mobile member disposed in the space between the endplate components, the member being unconnected and free to move from side-to-side within the space; and
    one or more elongated, partially elastic elements spanning the peripheral region, each element having two ends, one affixed to the upper endplate component, and another affixed to the lower endplate component to keep the mobile member from sliding out of the space at least in the anterior direction.

7. Apparatus for stabilizing an artificial disc replacement (ADR) of the type wherein a mobile member is disposed between opposing upper and lower vertebrae having endplates with anterior, lateral, and posterior peripheral regions, the apparatus comprising:
    one or more elongated elements spanning the peripheral region, each element having two ends, one affixed to the upper end plate and/or vertebrae, and another affixed to the lower end plate and/or vertebrae; and
    wherein the elements are tightened in-situ.

8. A method of stabilizing an artificial disc replacement (ADR), comprising the steps of:
    installing a mobile member between opposing upper and lower vertebrae having endplates having anterior, lateral, and posterior peripheral regions; and
    attaching one or more elongated elements across at least one of the peripheral regions after the mobile member is in place.

9. The method of claim 8, wherein the elongated elements span only the anterior region.

10. The method of claim 8, further including the step of tightening the elements following attachment.

11. The method of claim 8, wherein each elongated element has two ends, one affixed to the upper end plate and/or vertebrae, and another affixed to the lower end plate and/or vertebrae.

* * * * *